(12) United States Patent
 Takemura

(10) Patent No.: US 10,960,445 B2
(45) Date of Patent: Mar. 30, 2021

(54) WOOD CHIP FERMENTATION DEVICE

(71) Applicant: TAKEMURA ENGEI CO., LTD., Hamamatsu (JP)

(72) Inventor: Junichi Takemura, Hamamatsu (JP)

(73) Assignee: TAKEMURA ENGEI CO., LTD., Shizuoka (JP)

( * ) Notice: Subject to any disclaimer, the term of this patent is extended or adjusted under 35 U.S.C. 154(b) by 138 days.

(21) Appl. No.: 16/317,908

(22) PCT Filed: Jul. 15, 2016

(86) PCT No.: PCT/JP2016/071010
§ 371 (c)(1),
(2) Date: Jan. 15, 2019

(87) PCT Pub. No.: WO2018/011980
PCT Pub. Date: Jan. 18, 2018

(65) Prior Publication Data
US 2020/0376525 A1 Dec. 3, 2020

(51) Int. Cl.
*B09B 3/00* (2006.01)

(52) U.S. Cl.
CPC ................. *B09B 3/0083* (2013.01)

(58) Field of Classification Search
None
See application file for complete search history.

(56) References Cited

FOREIGN PATENT DOCUMENTS

| JP | 1995251146 A | 10/1995 |
|----|---|---|
| JP | 1996057448 A | 3/1996 |
| JP | 2010255996 A | 11/2010 |
| JP | 2012019781 A | 2/2012 |
| JP | 2016034603 A | 3/2016 |

*Primary Examiner* — Derek N Mueller
(74) *Attorney, Agent, or Firm* — Browdy and Neimark, PLLC

(57) ABSTRACT

A wood chip fermentation device includes: a chip fermenter 11 that is charged with wood chips serving as a heat source and that ferments the wood chips; a temperature sensor 11a that is provided inside the chip fermenter 11 and measures the temperature inside the chip fermenter; a thermal energy extracting pipe 12 that is disposed inside the chip fermenter and extracts fermentation heat from inside the chip fermenter; a pump section 13 that supplies a medium to or takes out a medium from the thermal energy extracting pipe 12; a stirring blade 14a that stirs wood chips 10a put in the chip fermenter 11; and a discharge conveyor 15 that is disposed at a lower portion of the chip fermenter 11 and discharges fermented material. The stirring blade 14a is disposed between the thermal energy extracting pipes 12 and a rotating surface thereof is in a state of being parallel to the thermal energy extracting pipes 12. A bottom surface of the chip fermenter 11 is formed in an arcuate shape such as to follow the rotating outer peripheral surface of the stirring blade 14a. A plurality of temperature sensors 11a are installed in a vertical direction inside each chip fermenter. Control of an on-off valve of the thermal energy extracting pipe 12 is performed based on temperature information from the temperature sensors 11a.

4 Claims, 5 Drawing Sheets

[FIG. 1]
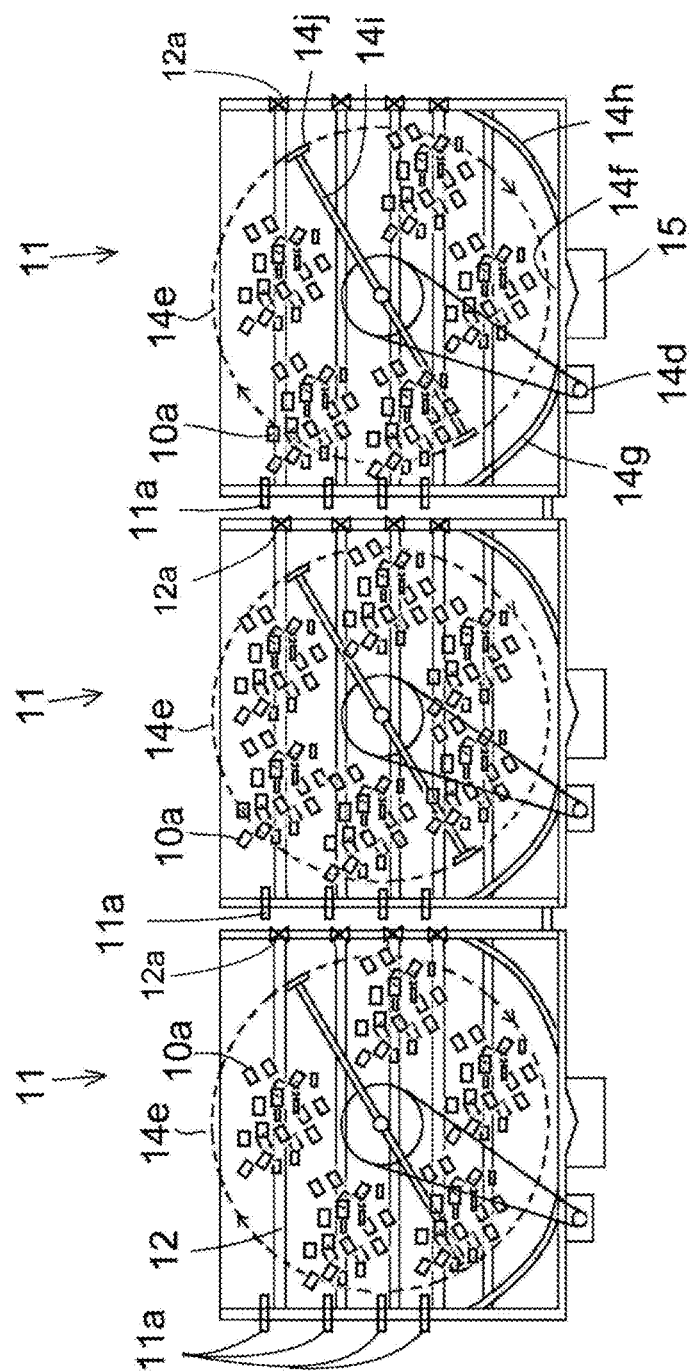

[FIG. 2]
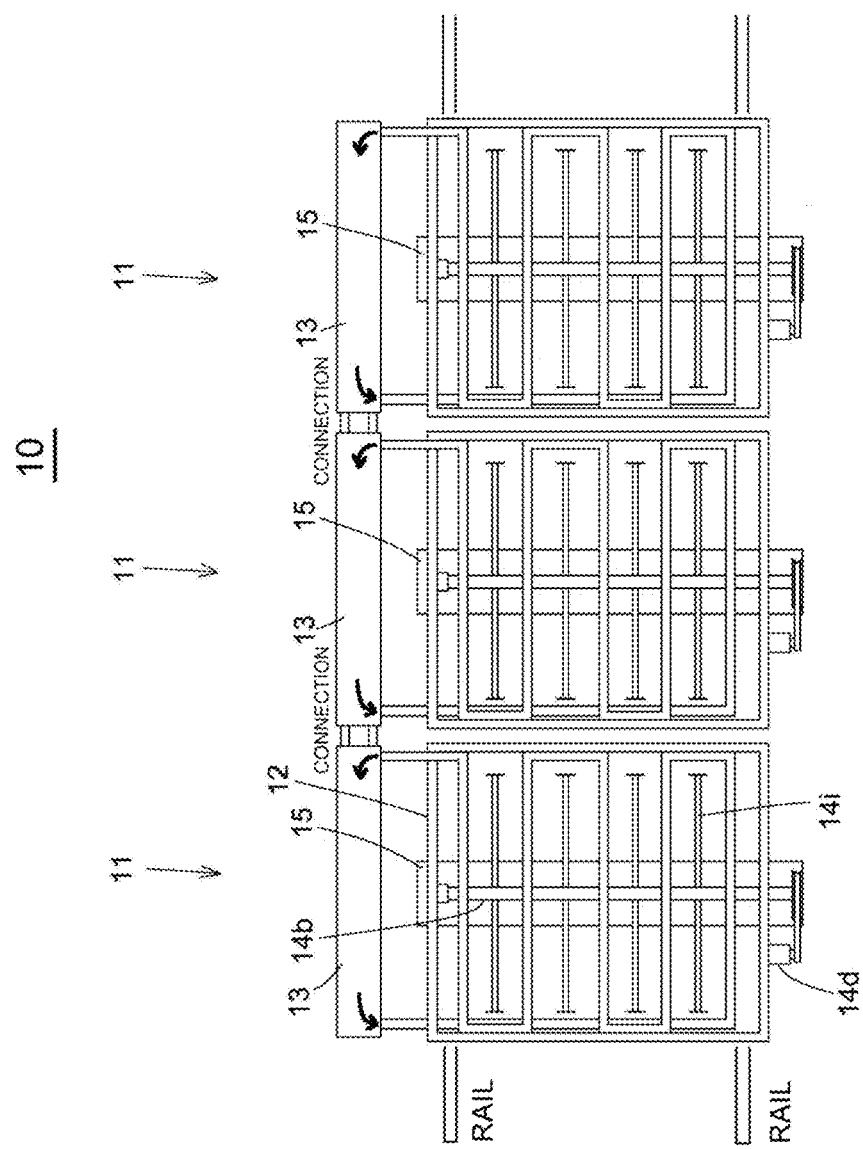

[FIG. 3]
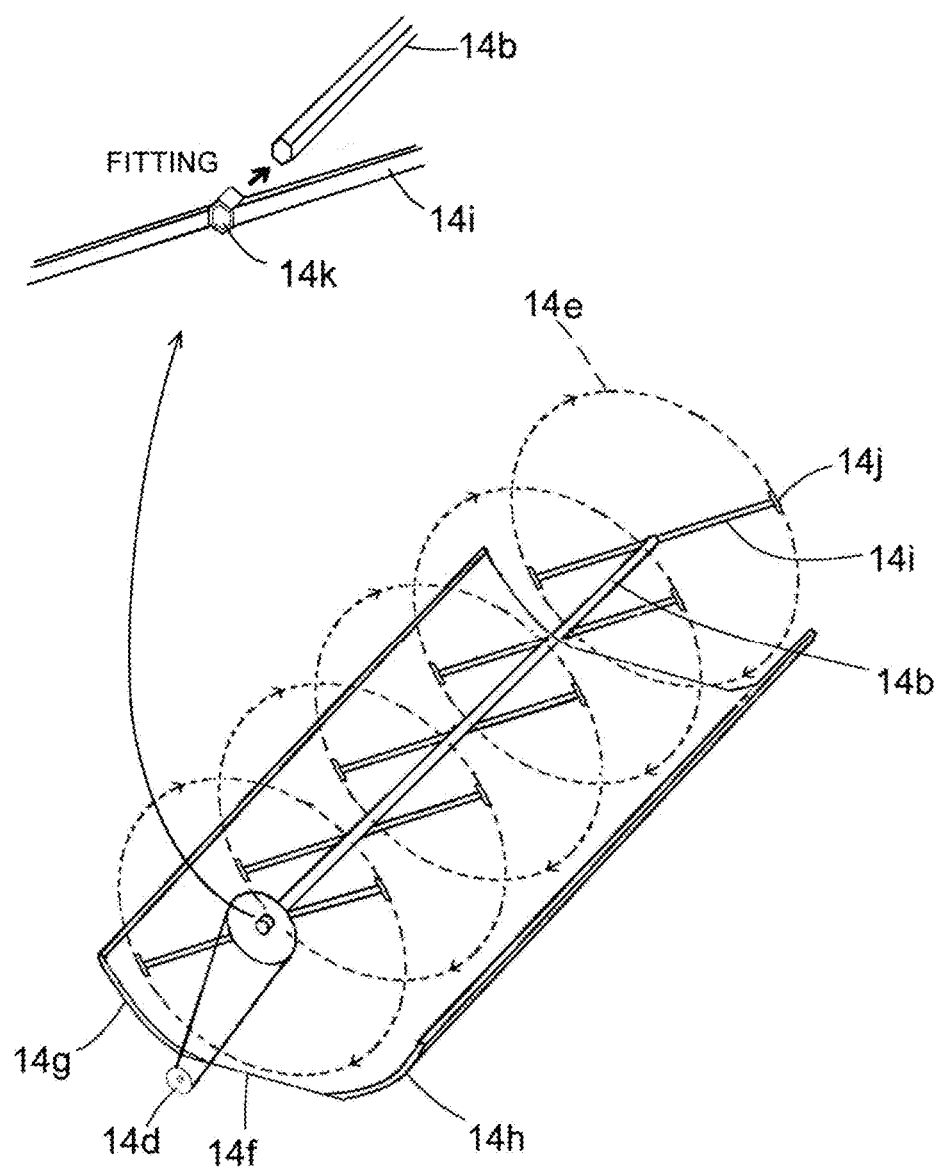

[FIG. 4]
(a)
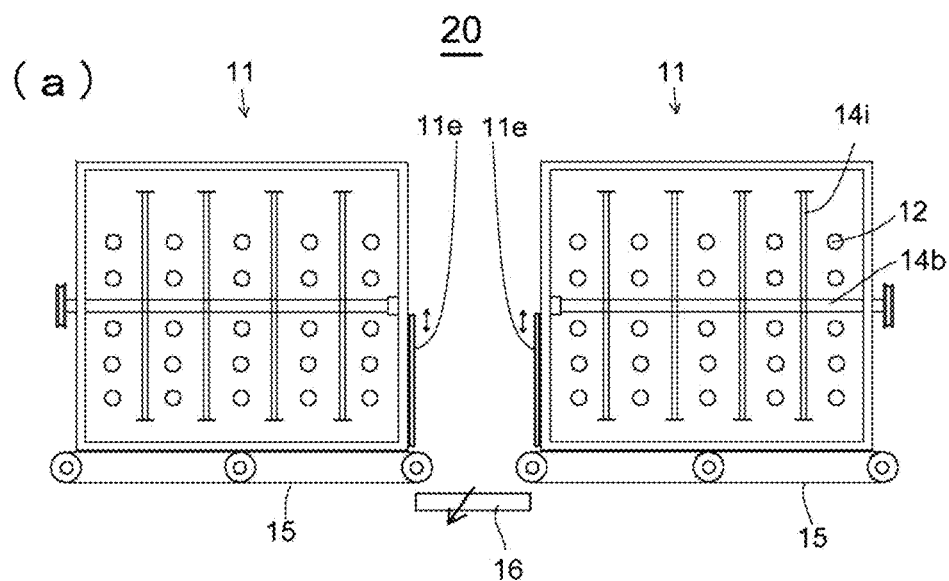
(b)
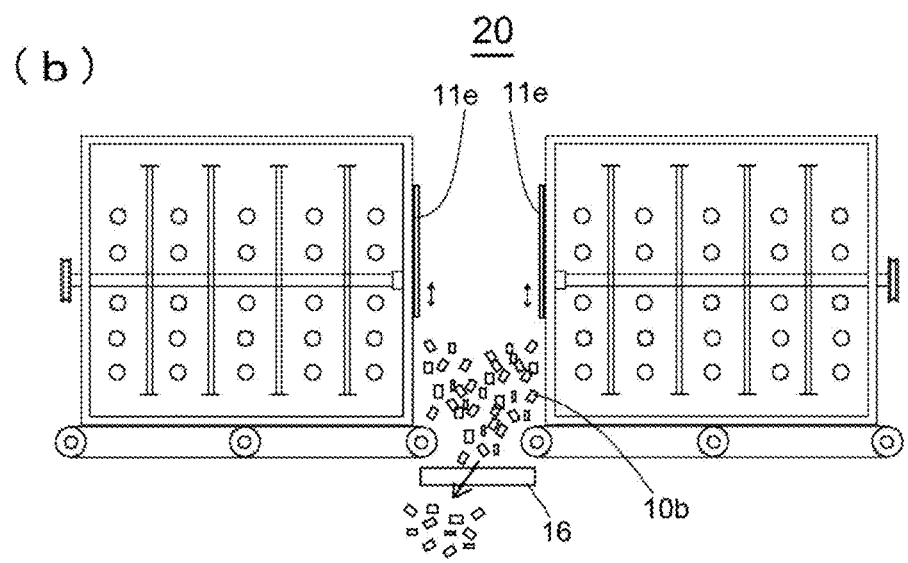

[FIG. 5]
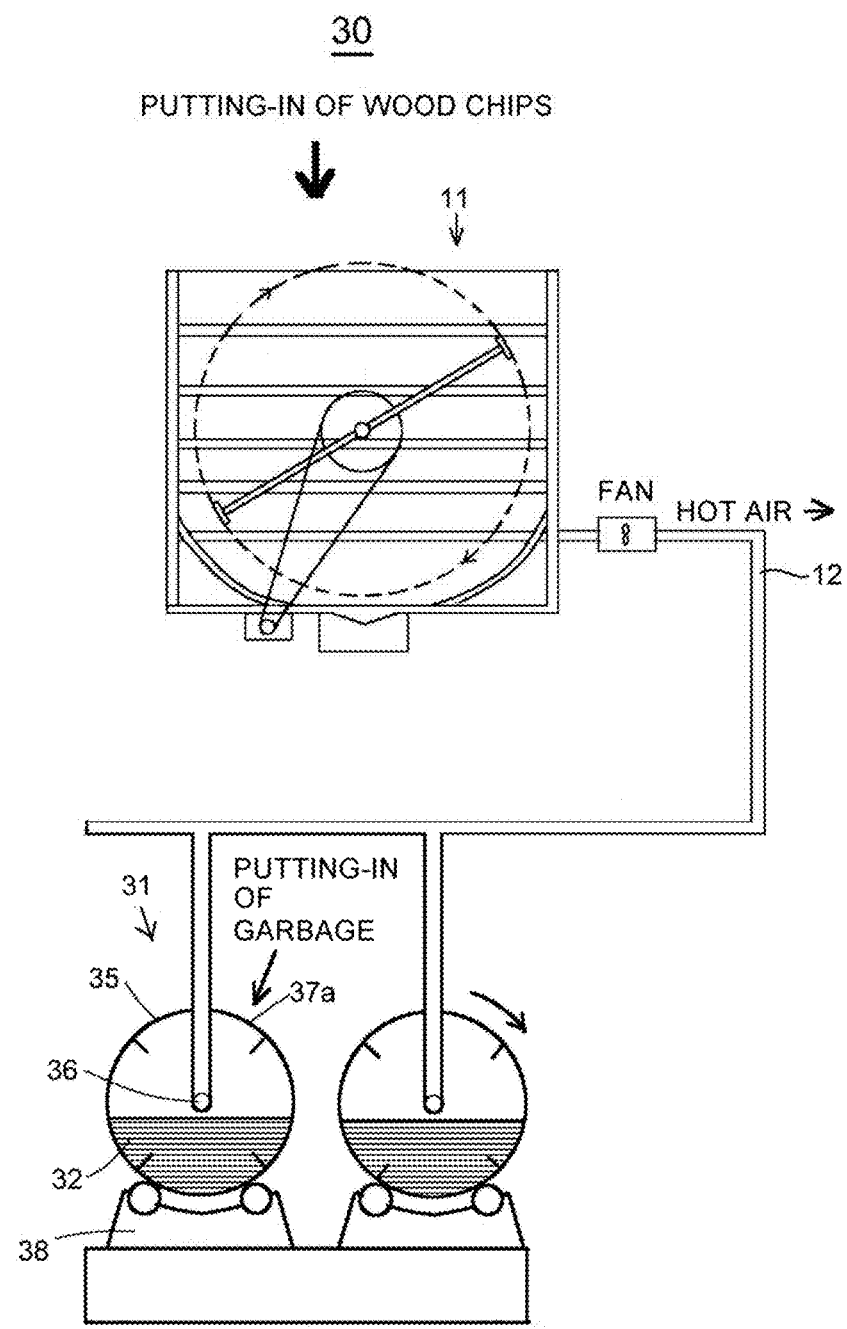

WOOD CHIP FERMENTATION DEVICE

TECHNICAL FIELD

The present invention relates to a wood chip fermentation device in which wood chips such as tree trimming wastes generated by garden plant pruning, tree trimming or the like are fermented, the fermentation heat is heat-exchanged with water or air, and the resulting hot water or hot air is circulated for utilization.

BACKGROUND ART

In the past, in greenhouses for use in raising seeding, cultivation and the like, heating has been conducted by combustion of heavy oil or the like. In this case, however, there are problems such as a considerable fuel cost, and bad influences on the environment such as emission of a large quantity of carbon dioxide gas. In addition, in the heating of a greenhouse, the supply temperature at the house inlet is a comparatively high temperature and hot air is circulated by a fan or the like, so that a temperature difference is generated between the vicinity of the fan and areas far from the fan, which may influence the growth of crop.

In view of this, as a system for fermenting various kinds of organic wastes and utilizing the fermentation heat, instead of the heating by combustion of heavy oil or the like, there have been proposed various systems.

For example, an organic waste treatment system described in PTL 1 includes an organic waste crushing and mixing section, and a fermenting and composting tank having a device for pressurizing and stirring the organic wastes, in which a metallic piping is arranged at side walls of the fermenting and composting tank, cooling water is passed through the piping for heating, and the resulting hot water is circulated in a building for heating. In this system, in addition to the production of fermented compost, the hot water obtained utilizing the fermentation heat is supplied to a greenhouse.

CITATION LIST

Patent Literature

[PTL 1]
 JP 2006-111479A

SUMMARY

Technical Problems

In such a system, however, it is necessary to provide equipment such as a crushing and mixing device and a pressurizing device, which leads to a large-scale equipment.

Further, huge electric power is required for operating various devices, and problems still remain from the viewpoint of ecology which has been particularly desired in recent years.

The present invention has been made in order to solve the above-mentioned problems. Accordingly, it is an object of the present invention to provide a wood chip fermentation device in which equipment can be configured in a compact form, which performs fermentation of wood chips and is friendly to the environment, and which is excellent in operation controllability.

In addition, it is another object of the present invention to provide a wood chip fermentation device in which wood chip fermenters are unitized and can be easily connected with and separated from one another, and which has a size conforming to the object.

Further, the present invention is for contriving to make the wood chip fermentation device efficient by transferring thermal energy between the connected wood chip fermenters.

Solution to Problems (1) A wood chip fermentation device of the present invention includes: a chip fermenter 11 that is charged with wood chips serving as a heat source and ferments the wood chips; a temperature sensor 11a that is provided inside the chip fermenter 11 and measures a temperature inside the chip fermenter; a thermal energy extracting pipe 12 that is disposed inside the wood fermenter and extracts fermentation heat from inside the chip fermenter; a pump section 13 that supplies a medium to or takes out a medium from the thermal energy extracting pipe 12; a stirring blade 14a that stirs wood chips 10a put in the chip fermenter 11; and a discharge conveyor 15 that is disposed at a lower portion of the chip fermenter 11 and discharges fermented material.

The stirring blade 14a is disposed between the thermal energy extracting pipes 12, and a rotating surface thereof is in a state of being parallel to the thermal energy extracting pipe 12, a bottom surface of the chip fermenter 11 is formed in an arcuate shape such as to follow a rotating outer peripheral surface of the stirring blade 14a. A plurality of the temperature sensors 11a are installed in a vertical direction inside the chip fermenter, and control of an on-off valve of the thermal energy extracting pipe 12 is performed based on temperature information from the temperature sensors 11a.

(2) The wood chip fermentation device of the present invention is characterized in that, in the above paragraph (1), two wood chip fermentation devices are arranged to face each other, and a fermented material 10b of the wood chips taken out from facing lower portions of the chip fermenters 11 onto a carrying-out conveyor 16 by the discharge conveyor 15 is further taken out to the exterior by the carrying-out conveyor 16.

(3) The wood chip fermentation device of the present invention is characterized in that, in the above paragraph (1) or (2), a garbage treatment device 21 is further jointly provided which includes: a tubular rotary body 25 that is disposed horizontally and capable of rotating; and a hot air introduction pipe 26 passed inside the rotary body, and hot air taken out from the pump section 13 is fed into the rotary body 25, to dry the garbage in the rotary body 25 and to accelerate fermentation of the garbage.

(4) The wood chip fermentation device of the present invention is characterized in that, in any one of the above paragraphs (1) to (3), a plurality of the chip fermenters 11 are disposed on rails such that the chip fermenters 11 can be connected to and separated from one another.

Advantageous Effects of Invention

The wood chip fermentation device of the present invention includes: the chip fermenter 11 that is charged with wood chips serving as a heat source and ferments the wood chips; the temperature sensor 11a that is provided inside the chip fermenter 11 and measures the temperature inside the chip fermenter; the thermal energy extracting pipe 12 that is disposed inside the wood fermenter and extracts fermentation heat from inside the chip fermenter; the pump section 13 that supplies a medium to or takes out a medium from the thermal energy extracting pipe 12; the stirring blade 14a that stirs the wood chips 10a put in the chip fermenter 11; and the discharge conveyor 15 that is disposed at a lower portion of the chip fermenter 11 and discharges fermented material.

The stirring blade is disposed between the thermal energy extracting pipes 12, and the rotating surface thereof is in the state of being parallel to the thermal energy extracting pipe 12, the bottom surface of the chip fermenter 11 is formed in an arcuate shape such as to follow the rotating outer peripheral surface of the stirring blade 14a. A plurality of the temperature sensors 11a are installed in the vertical direction inside the chip fermenter, and control of the on-off valve of the thermal energy extracting pipe 12 is performed based on temperature information from the temperature sensors 11a. Therefore, it is possible to contrive effective utilization of thermal energy produced by efficient fermentation of wood chips generated by garden plant pruning, tree trimming, farm work or the like.

In addition, by use of the thermal energy produced in the wood chip fermentation device, garbage can be dried and utilized as compost.

BRIEF DESCRIPTION OF DRAWINGS

FIG. 1 is a front view depicting a state in which three chip fermenter units of a wood chip fermentation device of Embodiment 1 are connected and wood chips are stirred.

FIG. 2 is a plan view depicting a state, as seen from above, of the wood chip fermentation device having the three chip fermenter units connected to one another of FIG. 1.

FIG. 3 is a perspective view depicting stirring blades of the wood chip fermentation unit of Embodiment 1.

FIG. 4 depicts sectional views depicting a wood chip fermentation device of Embodiment 2, in which (a) depicts a state of a fermenting operation, and (b) depicts a state after the fermenting operation is finished.

FIG. 5 is a schematic illustration of a wood chip fermentation device of Embodiment 3.

DESCRIPTION OF EMBODIMENTS

Embodiment 1

A wood chip fermentation device 1 according to Embodiment 1 of the present invention is a system utilizing natural heat generation energy obtained by fermenting, as a raw material, wastes such as wood chips generated after garden plant pruning or the like.

The wood chip fermentation device of Embodiment 1 is a device by which natural heat generation energy obtained by charging a chip fermenter with wood chips arising from garden plant pruning, tree trimming or the like and fermenting the wood chips is extracted as thermal energy of hot air, hot water or the like and the thermal energy is supplied to the exterior.

In addition, when a fermented material obtained at the end of fermentation of wood chips after the lapse of approximately half year, for example, is taken out from the lower side of a chip fermenter and utilized as compost, the fermented material can be returned to the nature, so that wasteful consumption of resources is avoided.

As illustrated in FIGS. 1 to 3, the wood chip fermentation device 10 according to Embodiment 1 includes: chip fermenters 11 supplied with wood chips serving as a heat source; thermal energy extracting pipes 12 that are disposed inside the chip fermenters 11 and extract fermentation heat from inside the chip fermenters 11; pump sections 13 by which air or water as a medium is supplied to or taken out from the thermal energy extracting pipes 12; stirring devices 14 having stirring blades for stirring wood chips 10a in the chip fermenters 11; and discharge conveyors 15 that are disposed at lower portions of the chip fermenters 11 and discharge the fermented material obtained upon the end of fermentation of the wood chips 10a.

According to the wood chip fermentation device 10 configured as above, fermentation heat obtained by fermentation of the wood chips 10a can be extracted to the exterior through the thermal energy extracting pipes 12, and can be utilized in various ways as a heat source in the exterior. For example, heating in raising seeding facilities, greenhouses and the like which has hitherto relied on petroleum or electricity can depend on this thermal energy, leading to a great economic effect.

In addition, when the wood chips (fermented material) fermented upon the end of fermentation of the wood chips 10a after half year or one year are taken out by the discharge conveyors 15 and used as compost, the wood chips (fermented material) can be returned to the nature, so that wasteful consumption of resources is avoided.

<Chip fermenter>

The chip fermenter 11 is a vessel for fermenting the wood chips 10a such as tree trimming wastes generated by garden plant pruning, tree trimming or the like. The wood chips 10a are crushed down to a predetermined size by a crusher or the like, and put into the chip fermenter 11. Note that the raw material put into the chip fermenter 11 is not limited to wood chips but may be farm wastes or the like in a predetermined size which can be fermented.

In addition, while only one chip fermenter 11 may be used, use of a plurality of chip fermenters disposed in a connected state is desirable from the viewpoint of stable supply of the thermal energy or fermented material produced. For example, where a plurality of chip fermenters 11 are charged with the wood chips 10a serving as a raw material at time intervals and are sequentially put into fermentation, it is possible, after the end of fermentation in one chip fermenter, to obtain fermentation heat from other chip fermenters, so that a stable thermal energy supply system can be realized.

Note that examples of the material for such a chip fermenter 11 include composite materials such as fiber-reinforced plastic (FRP), and stainless steel, aluminum and the like.

Besides, temperature sensors 11a are disposed inside each chip fermenter 11, and the temperature status inside the chip fermenter 11 is constantly monitored.

Note that where a single chip fermenter 11 of a minimum size is adopted as one unit, and a plurality of the units are connected, as required, to assemble a connected chip fermenter, the chip fermenter 11 can be enlarged according to the scale thereof.

<Stirring Device>

The chip fermenter 11 is provided with a stirring device 14 for accelerating fermentation of wood chips. The stirring device 14 is a rotary device having stirring blades 14a for stirring the wood chips 10a placed to fill the chip fermenter 11.

As illustrated, rotary shafts 14b of the stirring device 14 provided with the stirring blades 14a are arranged in a horizontal direction (width direction) inside the chip fermenters 11, and the rotary shafts 14b are connected to a stirring motor 14d by a belt 14c.

The rotary shafts 14b are rotationally driven at predetermined time intervals, to stir the wood chips 10a put in the chip fermenters 11, thereby accelerating a fermentation reaction. As for the timing of rotational driving of the stirring device 14, for example, the rotational driving is performed by obtaining a signal from a control device (not depicted) in the case where the temperatures of fermentation heat inside the chip fermenter 11 detected by the temperature sensors 11a are lowered. By this, fermentation of the wood chips 10a put in the chip fermenters 11 is promoted, whereby the temperatures in the chip fermenters 11 can be raised.

Note that the stirring blades 14a are disposed between the thermal energy extracting pipes 12 in such a manner that rotating surfaces 14e thereof are parallel to the thermal energy extracting pipes 12.

With the rotating surfaces 14e of the stirring blades 14a set parallel to the thermal energy extracting pipes 12, the stirring blades 14a do not interfere with the thermal energy extracting pipes 12 even when enlarged, so that large stirring blades can be disposed.

In addition, the thermal energy extracting pipes 12 also can be disposed densely in the vertical direction. Besides, as for the shape of a bottom surface 14f of the chip fermenter 11, curved portions 14g and 14h present at both sides of the bottom surface 14f are formed in an arcuate shape such that the shape of the bottom surface 14f follows an outer peripheral shape of the rotating surface 14e of the stirring blades 14a.

As a result, a dead zone in which non-stirred chips remain is absent at both sides of the bottom surface 14f, so that the wood chips can be efficiently made the most of.

Note that the stirring blade 14a has a structure in which a center of a rod-shaped portion 14i is fixed to the rotary shaft 14b, and stirring vanes 14j are provided at both tips of the rod-shaped portion 14i.

In addition, the shape of the rotary shaft 14b is a hexagonal prism as depicted in the enlarged view of FIG. 3, and a hexagonal frame 14k similar to the hexagonal prism and provided at a central portion of the stirring rod 14i is fitted to the hexagonal prism, to achieve secure fixation, whereby idling of the stirring vanes 14j relative to the rotary shaft 14b can be prevented, and the chips can be stirred more efficiently.

<Sprinkler>

In the case where fermentation of the wood chips 10a is accelerated and the temperature of the chip fermenter 11 is raised excessively, a sprinkler (not depicted) for sprinkling water to the chip fermenter 11 may be provided.

The sprinkler is a shower equipment for pouring water to the inside of the chip fermenter 11 in order to restrain the fermentation reaction of the wood chips 10a in the chip fermenter 11 and to lower the temperature of fermentation heat produced inside the chip fermenter 11.

<Thermal Energy Extracting Pipe>

The thermal energy extracting pipe 12 is a piping of a metal, a plastic or the like which is embedded inside the chip fermenter 11 charged with the wood chips 10a. By the fermentation heat in the periphery of the thermal energy extracting pipe 12, water or air or the like flowing in the thermal energy extracting pipe 12 is heated, and is taken out to the exterior through the pump section 13.

In addition, conversely, by suppling a medium heated in the exterior to the thermal energy extracting pipe 12 inside the chip fermenter 11 to raise the temperature inside the chip fermenter 11, the fermentation reaction of wood chips can be accelerated.

Note that the outside diameter of the thermal energy extracting pipes 12 is determined as required; in the fermenting device of Embodiment 1, thermal energy extracting pipes 12 with an outside diameter of approximately 10 to 100 mm are used in combination.

<Pump Section>

The pump section 13 is medium carrying means that is disposed in the chip fermenter 11 for supplying or taking out a medium in the thermal energy extracting pipe 12.

Note that for driving of the pump section 13, for example, a solar photoelectric generation panel or a battery or the like can be used as a power source.

<Temperature Sensor>

In each chip fermenter 11, the temperature sensors 11a for controlling the temperature inside the chip fermenter 11 are disposed. The temperature sensors 11a transmits the temperatures inside the chip fermenter 11 to the control device (not depicted). By this, the control device controls the fermentation state of the wood chips proceeding in each chip fermenter 11.

In addition, with the temperature sensors 11a disposed in each chip fermenter 11, it is possible, for example, to constantly obtain temperature information from the temperature sensors 11a disposed in each chip fermenter 11, and thereby to grasp the proceeding status of fermentation in each wood chip fermenter 11 with time. As a result, in the case where the temperature inside the chip fermenter is temporarily lowered to or below a predetermined temperature, the control device can drive the stirring device 14 such as to accelerate the fermentation reaction.

In addition, by suppling the thermal energy of a wood chip fermenter which fermentation has proceeded to a wood chip fermenter which fermentation is delayed, the fermentation reaction of wood chip fermenter which fermentation is delayed can be accelerated.

Further, for example, into one wood chip fermenter to be newly charged with wood chips 10a and put to fermentation, hot air inside the other wood chip fermenter in which fermentation has already proceeded may be introduced, whereby the fermentation reaction at the time of start-up of the one wood chip fermenter can be accelerated.

In such a case, the thermal energy extracting pipes 12 are laid independently on the basis of each wood chip fermenter, and the driving of the pump sections 13 is also performed on the basis of each wood chip fermenter.

Note that, as illustrated in FIG. 1, a plurality of the temperature sensors 11a may be disposed at positions in the vertical direction inside the wood chip fermenter 11. By this, fermenter temperature information at the positions in the vertical direction inside the wood chip fermenter 11 can be monitored. For example, in the case where the charging height of wood chips is lowered due to fermentation of the wood chips (the volume of the wood chips is lowered due to the progress of fermentation), the thermal energy extracting pipe 12 may be exposed from a state of being covered with the wood chips, and, in this case, a situation in which the medium in the thermal energy extracting pipe 12 is cooled may be generated.

Such a situation causes circulation of the medium to be performed inefficiently. In order to prevent such a situation, therefore, temperature information is obtained from the temperature sensors 11a set at positions in the vertical direction inside the wood chip fermenter 11 is obtained, and a control is performed to close an on-off valve 12a of the thermal energy extracting pipe 12 located at a position where the temperature is lower than a predetermine temperature.

On the other hand, in the case where temperature information from the temperature sensor 11a set at a position in the vertical direction inside the wood chip fermenter 11 has reached a predetermined temperature, a control is performed to open the on-off valve 12a for circulating the medium in the thermal energy extracting pipe 12.

<Discharge Conveyor>

The discharge conveyor 15 is a belt conveyor that is disposed at a lower portion of the chip fermenter 11 and discharges the fermented material obtained upon the end of fermentation inside the chip fermenter 11 from a lower portion of the chip fermenter 11.

Note that the discharge of the fermented material by use of the discharge conveyor 15 is facilitated when the discharge side of the chip fermenter 11 is a shutter wall 11e of a vertically movable type and the shutter wall is raised to open the lower side.

<Operation of Wood Chip Fermentation Device>

In the wood chip fermentation device of Embodiment 1, the fermented materials obtained upon the end of fermentation can be sequentially taken out from the lower portions of the chip fermenters 11 by the discharge conveyors 15. Then, new wood chips are put into the chip fermenters 11 from above, and production of the fermented material is performed again.

In addition, a configuration may be adopted in which, for example, a plurality of chip fermenters are sequentially charged with new wood chips at an interval of one week, and the timings of starting fermentation of the wood chips in the plurality of chip fermenters are set different from one another, and the fermented materials are sequentially taken out from the chip fermenters in which fermentation has ended.

<Operation at Normal Time>

Temperature information is obtained from the temperature sensors 11a provided inside the chip fermenters, and a configuration may be adopted in which in the case where the temperature inside the chip fermenter becomes not higher than a predetermined temperature (for example, not higher than 40° C.), the stirring blades are rotated to stir the wood chips in the chip fermenter, thereby accelerating the fermentation of the wood chips, whereas in the case where the temperature inside the chip fermenter becomes not lower than a predetermined temperature (for example, not higher than 80° C.), water is poured into the chip fermenter to restrain the fermentation of the wood chips. These predetermined temperatures are appropriately determined according to the embodiment.

Note that in the case where only a bottom portion of the chip fermenter is charged with wood chips and the fermenter is operated (in the case where a space is present at an upper portion of the chip fermenter, such as the case where a small amount of wood chips is used), operating only the thermal energy extracting pipes 12 located on the lower side is efficient as a thermal energy extracting method. In this case, the on-off valves 12a of the thermal energy extracting pipes 12 located on the upper side are automatically controlled to a closed state, based on the temperature information from the temperature sensors 11a.

On the other hand, in the case where the chip fermenter is charged with wood chips in the whole range in the height direction and the fermenter is operated, the on-off valves 12a of the thermal energy extracting pipes 12 on the upper side are automatically controlled to an open state, based on the temperature information from the temperature sensors 11a located on the upper side.

<End of Fermentation>

In the case where the temperature inside the chip fermenter 11 becomes not higher than a predetermined temperature (for example, not higher than 30° C.), it is determined that fermentation of the wood chips in the chip fermenter 11 has ended, and the discharge conveyor 15 disposed at a lower portion of the chip fermenter 11 is driven, to carry out the wood chips 10a in the chip fermenter 11 to the exterior. This predetermined temperature is appropriately determined according to the embodiment.

Embodiment 2

FIG. 4 illustrates a wood chip fermentation device according to Embodiment 2.

(a) is a state of a fermenting operation, and (b) is a state after a fermenting operation is finished.

A wood chip fermentation device 20 according to Embodiment 2 has a configuration in which two wood chip fermentation devices of Embodiment 1 are arranged to face each other, and a fermented material 10b of wood chips taken out from facing lower portions of the chip fermenters 11 onto a carrying-out conveyor 16 by the discharge conveyors 15 is further taken out to the exterior by the carrying-out conveyor 16. By providing such a carrying-out conveyor 16, the fermented material 10b produced by the plurality of wood chip fermentation devices can be efficiently carried out to the exterior.

Embodiment 3

FIG. 5 depicts a wood chip fermentation device according to Embodiment 3.

The wood chip fermentation device 30 according to Embodiment 3 is a system in which a garbage treatment device is jointly provided in addition to the wood chip fermentation device of Embodiment 1. Specifically, thermal energy of hot air, hot water or the like obtained by fermenting, as a raw material, wastes such as wood chips generated after garden plant pruning or the like is effectively utilized in the jointly provided garbage treatment device to treat garbage.

As depicted in FIG. 5, the wood chip fermentation device 30 according to Embodiment 3 has garbage treatment devices 31 provided jointly to the chip fermenter 11.

The garbage treatment device 31 includes a tubular rotary body 35 that is disposed horizontally and is rotatable, and a hot air introducing pipe 36 passed inside the rotary body 35, in which garbage is put into the rotary body 35, and hot air sent from the chip fermenter 11 is blown into the hot air introducing pipe 26, to accelerate drying and fermentation of the garbage in the rotary body 25.

Since mixing wood chips in an amount of approximately 10% based on the garbage instead of fermenting the garbage singly accelerates the fermentation of the garbage, it is preferable to mix wood chips.

In addition, mixing of wood chips causes the compost to have an appropriate volume, which ensures easy handling.

In the inside of the rotary body 35, hot air sent from the chip fermenter 11 is introduced into a hot air intake port 36a of the garbage treatment device 31, and is blown off into the rotary body 35 through a hole 36b opened in the hot air introducing pipe 36 passed inside the rotary body 35, to dry the garbage and promote fermentation.

In addition, a garbage putting-in port 37a is provided on one side in regard of a longitudinal direction of the rotary body 35, and garbage, wood chips, a fermenting agent and the like are put in therethrough. The hot air sent from the chip fermenter 11 is blown off into the rotary body 35 through the hole 36b opened in the hot air introducing pipe 36 passed inside the rotary body 35, to dry the garbage and promote fermentation.

The garbage upon completion of the treatment in the rotary body 35 by rotating the rotary body 35 a few times in one hour can be discharged through a garbage discharge port 37b provided on the other side in the longitudinal direction of the rotary body 35.

Note that a rotation bearing 38 fixed to a base is provided at a lower portion of the rotary body 35, to support the rotary body 35 and permit the rotary body 35 to rotate smoothly. In order that movement of the garbage inside the rotary body 35 is performed smoothly, a rotational center axis of the rotary body 35 is preferably set low and inclined to the garbage discharge port 37b side.

Thus, in the wood chip fermentation device 30 of Embodiment 3, a drying and fermenting treatment of garbage is conducted in the jointly provided garbage treatment device 31 by utilizing the thermal energy produced in the chip fermenter 11, so that a treatment cost for the garbage is low. In addition, an operation of mixing wood chips with garbage can be reduced.

Note that while a state in which two rotary bodies are disposed for two fermenters is illustrated in FIG. 5, the number, inside diameter, length and the like of the rotary bodies 35 are preferably changed appropriately according to the amount of garbage to be treated.

The hot air may be blown off directly into a garbage tank, or hot water may be sent to a jacket of the garbage tank.

Example

Use form of the wood chip fermentation device and an effect thereof in an example will be described further in detail below. Three chip fermenters 11 sized to be 2 mm in width, 3 m in length and 2 m in height were connected, the respective chip fermenters 11 were each charged with approximately 100 kg of wood chips and 10 kg of a fermenting agent such as rice bran or oil meal, and an operation of the wood chip fermentation device was started.

It is desirable to add the fermenting agent in an amount of approximately ⅟₁₀ based on the weight of the wood chips, since such an addition accelerates the fermentation of the wood chips.

After the lapse of 48 hours from the start of the operation, it was possible to take out hot water at 50° C. through the thermal energy extracting pipe 12.

INDUSTRIAL APPLICABILITY

The wood chip fermentation device of the present invention can realize effective utilization of thermal energy produced by fermenting wood chips generated upon garden plant pruning, tree trimming, farm work or the like.

In addition, the thermal energy produced in the wood chip fermentation device can be extracted to the exterior and utilized as various energy sources such as utilization for raising seeding devices, floor heating, turning bath water into hot water, open air bath, footbath, turning drinking water into hot water, house heating and the like.

Further, formation of compost (fermented material) using wood chips as a raw material can also be performed simultaneously, and, accordingly, the wood chip fermentation device of the present invention is very high in industrial applicability.

REFERENCE SIGNS LIST

10 Wood chip fermentation device of Embodiment 1
10a Wood chips
10b Fermented material of wood chips
11 Chip fermenter
11a Temperature sensor
11b Bottom surface of chip fermenter
11c, 11d Curved portion
11e Shutter wall
12 Thermal energy extracting pipe
12a On-off valve
13 Pump section
14 Stirring device
14a Stirring blade
14b Rotary shaft
14c Belt
14d Stirring motor
14e Rotating surface of stirring blade
14f Bottom surface of chip fermenter
14g, 14h Curved portions at both sides of bottom surface
14i Rod
14j Stirring vane
14k Fitting frame
15 Discharge conveyor
16 Carrying-out conveyor
20 Wood chip fermentation device of Embodiment 2
30 Wood chip fermentation device of Embodiment 3
31 Garbage treatment device
35 Rotary body
36 Hot air introducing pipe
36a Hot air intake port
36b Hole formed in hot air introducing pipe
37a Garbage putting-in port
37b Garbage discharge port
38 Rotation bearing

The invention claimed is:

1. A wood chip fermentation device comprising:
a chip fermenter 11 that is charged with wood chips serving as a heat source and ferments the wood chips;
a temperature sensor 11a that is provided inside the chip fermenter 11 and measures a temperature inside the chip fermenter;
a plurality of thermal energy extracting pipes 12 that are disposed inside the chip fermenter and extract fermentation heat from inside the chip fermenter;
a pump section 13 that supplies a medium to or takes out a medium from the thermal energy extracting pipe 12;
a stirring blade 14a that stirs wood chips 10a put in the chip fermenter 11; and
a discharge conveyor 15 that is disposed at a lower portion of the chip fermenter 11 and discharges fermented material,
wherein the stirring blade 14a is disposed between the thermal energy extracting pipes 12,
a rotating surface thereof is in a state of being parallel to the thermal energy extracting pipes 12,
a bottom surface of the chip fermenter 11 is formed in an arcuate shape such as to follow a rotating outer peripheral surface of the stirring blade 14a,
a plurality of the temperature sensors 11a are installed in a vertical direction inside the chip fermenter, and
control of an on-off valve of the thermal energy extracting pipe 12 is performed based on temperature information from the temperature sensors 11a.

2. The wood chip fermentation device according to claim 1,
wherein two chip fermenters 11 are arranged to face each other, and a fermented material 10b of the wood chips taken out from facing lower portions of the chip fermenters 11 onto a carrying-out conveyor 16 by the discharge conveyor 15 is further taken out to the exterior by the carrying-out conveyor 16.

3. The wood chip fermentation device according to claim 1, further jointly comprising:
    a garbage treatment device 31 which includes
    a tubular rotary body 35 that is disposed horizontally and capable of rotating, and
    a hot air introducing pipe 36 passed inside the rotary body, and
    hot air as the medium taken out from the pump section 13 being fed into the rotary body 35, to dry the garbage in the rotary body 35 and to accelerate fermentation of the garbage.

4. The wood chip fermentation device according to claim 1,
    wherein a plurality of the chip fermenters 11 are disposed on rails such that the chip fermenters 11 can be connected to and separated from one another.

\* \* \* \* \*